(12) United States Patent
Vogt

(10) Patent No.: US 6,440,239 B1
(45) Date of Patent: Aug. 27, 2002

(54) METHODS FOR MAKING ABSORBENT ARTICLES WITH SEPARATE LEG CUFFS AND WAIST PIECES

(75) Inventor: Robert Eugene Vogt, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/487,666

(22) Filed: Jan. 19, 2000

Related U.S. Application Data

(62) Division of application No. 08/771,601, filed on Dec. 20, 1996, now Pat. No. 6,017,406.

(51) Int. Cl.$^7$ .............................................. B32B 31/00
(52) U.S. Cl. ....................... 156/73.2; 156/164; 156/229; 156/263; 156/265; 156/269; 604/385.01; 604/385.04; 604/385.28; 604/385.29; 604/385.3
(58) Field of Search .................... 156/164, 163, 156/256, 263, 265, 269, 229, 73.1, 73.2, 73.3, 270; 604/385.01, 385.04, 385.28, 385.29, 385.3; 2/402

(56) References Cited

U.S. PATENT DOCUMENTS

| | | | |
|---|---|---|---|
| 3,400,718 A | 9/1968 | Saijo | 128/291 |
| 4,381,781 A | 5/1983 | Sciaraffa et al. | 604/372 |
| 4,711,693 A | 12/1987 | Holze, Jr. | 156/580.1 |
| 4,743,241 A | 5/1988 | Igaue et al. | 604/385 A |
| 4,808,177 A | 2/1989 | DesMarais et al. | 604/385.1 |
| 4,834,741 A | 5/1989 | Sabee | 604/385.2 |
| 4,861,652 A * | 8/1989 | Lippert et al. | 428/284 |
| 4,900,317 A | 2/1990 | Buell | 604/370 |
| 4,904,251 A | 2/1990 | Igaue et al. | 604/385.2 |
| 4,909,870 A | 3/1990 | Gould et al. | 156/66 |
| 4,917,696 A | 4/1990 | De Jonckheere | 604/385.2 |
| 4,968,313 A | 11/1990 | Sabee | 604/385.2 |
| 5,061,331 A | 10/1991 | Gute | 156/64 |
| 5,091,039 A | 2/1992 | Ujimoto et al. | 156/519 |
| 5,137,526 A | 8/1992 | Coates | 604/391 |
| 5,489,282 A | 2/1996 | Zehner et al. | 604/385.1 |
| 5,527,302 A * | 6/1996 | Endres et al. | 604/385.1 |
| 5,560,793 A | 10/1996 | Ruscher et al. | 156/73.1 |
| 5,584,954 A | 12/1996 | van der Klugt | 156/265 |

FOREIGN PATENT DOCUMENTS

| | | |
|---|---|---|
| EP | 0 528 282 A2 | 2/1993 |
| EP | 0 532 034 A2 | 3/1993 |
| GB | 2 214 057 A | 8/1989 |
| JP | 6-209968 | 8/1994 |
| WO | WO 95/34265 | 12/1995 |
| WO | WO 96/15749 | 5/1996 |
| WO | WO 96/23470 | 8/1996 |
| WO | WO 96/24319 | 8/1996 |
| WO | WO 96/38116 | 12/1996 |

* cited by examiner

*Primary Examiner*—Linda Gray
(74) *Attorney, Agent, or Firm*—Wilhelm Law Service; Thomas D. Wilhelm

(57) ABSTRACT

The invention relates to methods of fabricating absorbent articles. In a method of the invention, a bodyside liner, an absorbent core, and an outer cover are joined to form an absorbent article web sausage. Leg cut-outs are cut on opposing sides of the web sausage, and a waist opening is cut in a central region of the web sausage. Adhesive is applied to one of (i) a waist piece material and (ii) the web sausage about the waist opening; and also to one of (iii) extensible leg cuff material and (iv) the web sausage adjacent the leg cut-outs. A waist piece is severed from waist piece material, and is placed. over the waist opening and secured to the web sausage. Leg cuffs are severed from the leg cuff material, and are placed over the leg cutouts and secured to the web sausage. The waist piece and leg cut-outs are preferably stretched to a dimension representing about 5% to about 95% of stretch-to-stop dimensions when bonded to the web sausage.

11 Claims, 4 Drawing Sheets

METHODS FOR MAKING ABSORBENT ARTICLES WITH SEPARATE LEG CUFFS AND WAIST PIECES

CROSS-REFERENCE TO RELATED APPLICATIONS

This application is a divisional of application Ser. No. 08/771,601 filed Dec. 20, 1996, now U.S. Pat. 6,017,406.

FIELD OF THE INVENTION

The present invention relates to methods for fabricating absorbent articles, including applying selected material to an absorbent article web sausage. More particularly, the methods include cutting a waist opening in the web sausage and applying a waist piece to cover the waist opening. The methods further include cutting leg cut-outs on each side of the web sausage and applying leg cuffs to cover the leg cut-outs.

BACKGROUND OF THE INVENTION

Conventional methods of making absorbent articles, such as disposable diapers are well known in the art These methods usually rely on attaching leg cuffs, containment flaps, and other elements to the absorbent article as continuous webs of attachment material. Thus a .continuous strip of material, such as leg cuff material, is continuously applied to the shell of an absorbent article. This simple method allows for high speed forming of absorbent articles. Since material is continuously applied to the absorbent article shell, a portion of the material may be wasted or unnecessarily applied to portions of the absorbent article where it is not required. Further, the overall design and appearance of the absorbent article is limited by this method of manufacture.

In previous proposals, cuff materials were intended to be placed between the liner and the outer cover material. The difficulty of this proposal was that cutouts had to be cut in both the bodyside liner and the outer cover material prior to lamination and then accurately registered to entrap the cuff material. This process was considered too difficult to be cost effective and therefore was never practiced commercially. Applicant's process greatly reduces the complexity by placing waist and leg cuffs on an absorbent article web sausage after the bodyside liner, absorbent core and outer cover have been integrally secured to each other with the leg and/or waist openings cut out to form the unitary web sausage prior to cuff application.

SUMMARY OF THE DISCLOSURE

Methods for making a series of absorbent articles from an absorbent article web sausage are disclosed. A first embodiment comprises the steps of cutting at least one waist opening in a central region of the web sausage; applying adhesive to one of a waist piece material, and the web sausage about the waist opening; placing the waist piece material on a waist piece applicator and cutting the waist piece material to sever a waist piece therefrom, the waist piece having dimensions sufficiently large to cover at least one dimension of the waist opening; placing the waist piece over the waist opening; and securing the waist piece to the web sausage.

In most embodiments, the method includes moving the web sausage along a processing line on a conveyor, the conveyor supporting the web sausage before the waist piece is applied to the web sausage.

In some embodiments, the method includes the step of severing the web sausage in a direction substantially transverse to the length of the web sausage and across the waist piece, thereby severing, from the web sausage, an absorbent article including a portion of the waist piece. The remainder of the waist piece remains with the web sausage. The portion of the waist piece remaining with the web sausage forms a respective front waist or rear waist portion for the next successive absorbent article in the web sausage.

In most embodiments, the steps are repeated for individual sections of the web sausage to form a series of absorbent articles that are severed from the web sausage.

In some embodiments, the method includes placing waist pieces over spaced waist openings, the waist pieces being spaced from each other on the web sausage.

In most embodiments, the method includes the step of stretching the waist pieces, and securing the waist pieces to the waist openings in the stretched condition. The waist pieces preferably are stretched to a dimension representing about 5% to about 95% of the respective stretch-to-stop dimensions.

In some embodiments, the method includes ultrasonic bonding that finishes raw edges of the waist piece.

In some embodiments, the method includes moving the web sausage along a processing line from a first work station to a second work station to perform at least one step subsequent to cutting the waist opening.

Another embodiment discloses a method of applying leg cuffs to an absorbent article web sausage comprising the steps of: cutting leg cut-outs on opposing sides of the web sausage; applying adhesive to the extensible leg cuff materials and the web sausage adjacent the leg cut-outs; placing the extensible leg cuff materials on a leg cuff applicator and cutting the extensible leg cuff materials to sever extensible leg cuffs therefrom, the leg cuffs having dimensions longer than the lengths of the leg cut-outs; placing the extensible leg cuffs over the leg cut-outs; and securing the extensible leg cuffs to the web sausage.

In some embodiments, the method includes placing leg cuffs over spaced ones of the leg cut-outs, the leg cuffs being spaced from each other along the length of the web sausage on the processing line. The method can also include the step of stretching the leg cuffs, and applying the leg cuffs on the leg cut-outs in the stretched condition. The leg cuffs preferably are stretched to a dimension representing about 5% to about 95% of the respective stretch-to-stop dimensions.

In yet another embodiment, the invention comprehends a method for making an absorbent article comprising the steps of: joining a bodyside liner, an absorbent core, and an outer cover to form an absorbent article web sausage; cutting leg cut-outs on opposing sides of the web sausage and cutting a waist opening in the web sausage; applying adhesive to one of a waist piece material, and the web sausage about the waist opening; placing the waist piece material on a waist piece applicator and cutting a waist piece to a set of dimensions sufficiently large to cover the waist opening; placing the waist piece over the waist opening; and securing the waist piece to the web sausage.

Figure 1:
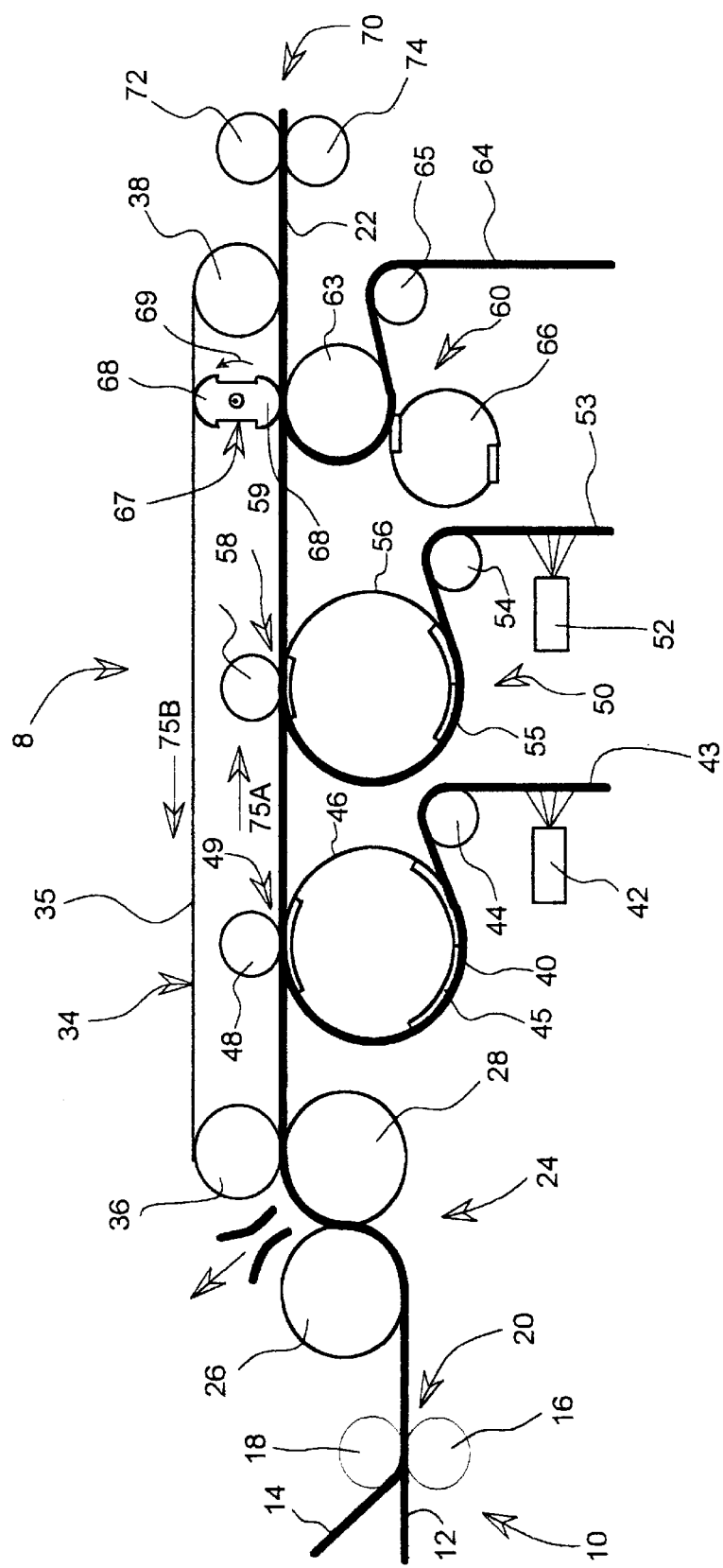
FIG. 1 shows a representative side elevation of apparatus for making successive absorbent articles.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

The present invention will be described herein as a method to produce absorbent articles, particularly disposable absorbent articles. The articles can be placed against or in proximity to the body of a wearer to absorb and contain various exudates discharged from the body. The method forms absorbent articles from an absorbent article web sausage.

Figure 2:
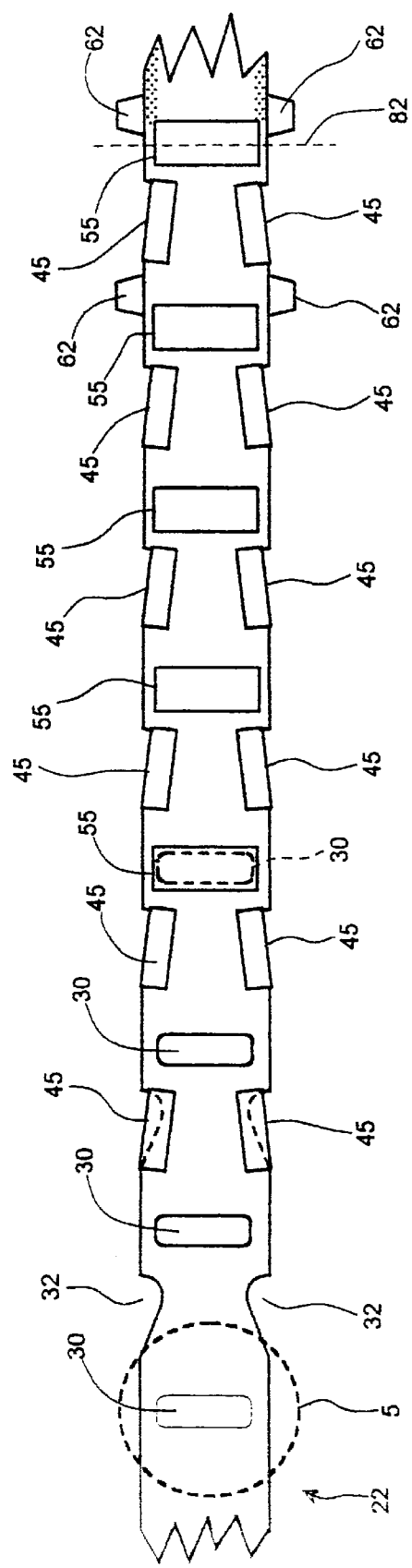
FIG. 2 shows a top view of an absorbent article web sausage which is the workpiece of the invention.

FIG. 1 shows an absorbent article assembly system 8. System 3 includes a compression nip device 10 that secures a bodyside liner 12 and an absorbent core 13 to (shown in FIG. 3) to an outer cover 14. Compression nip device 10 comprises first and second anvil rolls 16, 13 forming a first nip 20. First nip 20 applies pressure to the bodyside liner 12, outer cover 14, and absorbent core 13 therebetween, to form an absorbent article web sausage 22. Absorbent article web sausage 22 then moves to die cutter 24. Die cutter 24 includes an anvil roll 26 and a knife roll 28. Die cutter 24 cuts out a waist opening 30 and leg cut-outs 32 on web sausage 22 as shown in FIG. 2. Web sausage 22 is then transferred to a vacuum conveyor 34, which has an endless vacuum belt 35 mounted about end rolls 36, 38. Vacuum conveyor 34 transports web sausage 22 to a leg cuff applicator 40. Leg cuff applicator 40 includes a glue gun 42 that applies glue to leg cuff material 43, as shown in FIG. 1, or to web sausage 22 adjacent leg cut-outs 32. Idler roll 44 ensures even tension in leg cuff material 43. Leg cuff applicator 40 includes a variable velocity vacuum roll 46 that supports leg cuffs 45 and an anvil roll 48 that forms a second nip 49 with vacuum roll 46. A hot knife (not shown) on vacuum roll 46 cuts leg cuffs 45 to a size preferably greater than the opening of leg cut-outs 32. Leg cuff applicator 40 then secures leg cuffs 45 to the absorbent article web sausage 22.

A waist piece applicator 50 including a glue gun 52 then applies glue-to waist piece material 53, as shown in FIG. 1, or to web sausage 22 about waist opening 30. Idler roll 54 keeps waist piece material 53 at an even tension until it is cut into waist piece 55. Waist piece applicator 50 includes a variable velocity vacuum roll 56 supporting waist piece 55 and an anvil roll 58 forming a third nip 59 where the waist piece is applied to the web sausage. Waist piece 55 is cut or otherwise prepared for placement onto web sausage 22. After application of waist piece 55, web sausage 22 advances along conveyor 34 to an ear applicator 60. Ear applicator 60 secures ears 62 for folding or closing the absorbent article or for mounting the absorbent article to a user. Ear applicator 60 includes a transfer or vacuum roll 63 which supports ears 62 and a knife roll 66. Knife roll 66 cuts ears 62 from ear material 64 fed around idler roll 65. An elliptical rotary stomper 67 with pucks 68 intermittently forms a nip with transfer roll 63 to place ears 62 on web sausage 22. An ultrasonic bonder 70, then finishes and smoothens the leg cuffs and/or waist piece to web sausage 22. Ultrasonic bonder 70 includes an anvil roll 72 and preferably a rotary ultrasonic horn 74. Containment flaps or other elements, of course, can also be added to complete manufacture of the absorbent articles.

Bodyside liner 12 may be manufactured from a wide selection of web materials, such as porous foams, reticulated foams, apertured plastic films or natural fibers. For example, bodyside liner 12 may comprise wood or cotton fibers. Other possible materials are synthetic fibers, such as polyester or polypropylene fibers, or a combination of natural and synthetic fibers. Bodyside liner 12 is suitably utilized to help isolate, from the wearer's skin, the liquids held in absorbent core 13.

Various woven and nonwoven fabrics can be used for bodyside liner 12. For example, bodyside liner 12 may be composed of a meltblown or spunbonded web of polyolefin fibers. Bodyside liner 12 may also comprise a carded and/or bonded web composed of natural and/or synthetic fibers. Bodyside liner 12 may also be composed of a substantially hydrophobic material wherein the hydrophobic material is treated with a surfactant or otherwise processed to impart a desired level of wettability and hydrophilicity.

In a particular embodiment of the present invention, bodyside liner 12 may comprise a spunbonded polypropylene fabric composed of about 2.8–3.2 denier fibers formed into a web having a basis weight of about 22 grams per square meter and a density of about 0.06 grams per cubic centimeter. The fabric is treated with about 0.3 weight percent of a surfactant.

Bodyside liner 12 may comprise a multiplicity of components, layers, or partial layers. which correspond to any of the materials disclosed herein, as well as others known in the art.

Absorbent core 13 suitably comprises a matrix of hydrophilic fibers, such as a web of cellulosic fluff, preferably in combination with a high-absorbency material commonly known as superabsorbent material. In a particular embodiment, absorbent core 13 comprises a mixture of superabsorbent hydrogel-forming particles and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent core.

Alternatively, absorbent core 13 may comprise a laminate of fibrous webs and superabsorbent material or other suitable means of maintaining a superabsorbent material in a localized area.

Figure 3:
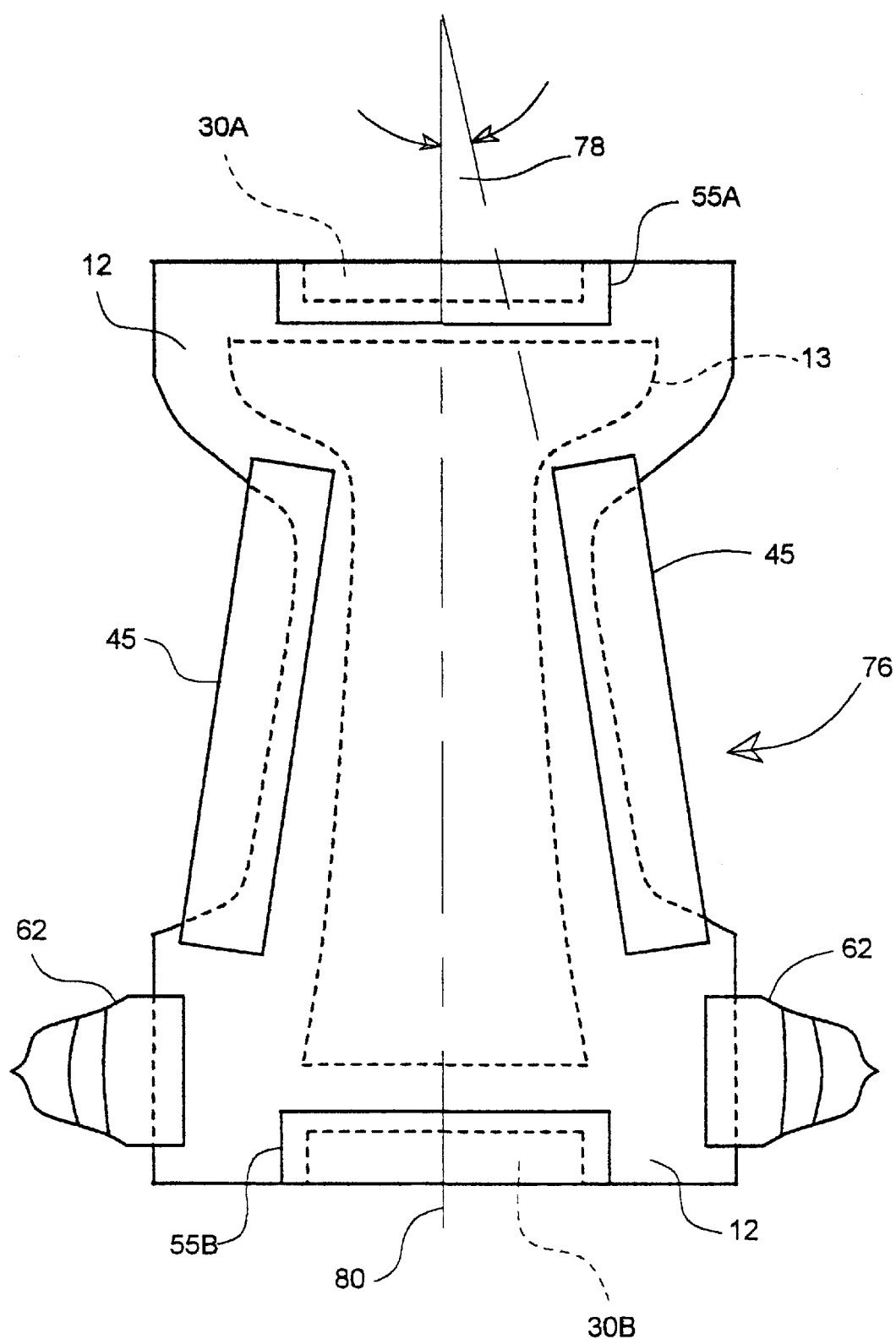
FIG. 3 shows a plan view of an absorbent article formed with the web sausage of FIG. 2, using the apparatus of FIG. 1.

Absorbent core 13 can have any of a number of shapes. For example, the absorbent core may be rectangular, T-shaped or I-shaped. It is generally preferred that the absorbent core be narrower in the crotch portion than in the rear and/or front portions. As shown in FIG. 3, absorbent core 13 generally does not extend over the entire dimensions of outer cover 14 or bodyside liner 12.

The high-absorbency material in absorbent core 13 can be selected from natural, synthetic and modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable, whereby absorbent properties are available but the swelled material is substantially immobile after absorbing water-based liquids. Such means can include, for example, physical entanglement crystalline domains, covalent bonds, ionic complexes and associations, hydrophilic associations such as hydrogen bonding, and hydrophobic associations or Van der Waals forces.

Outer cover 14 can be formed from a single layer, or from multiple components, layers, or partial layers, of material, such that the resulting outer cover is substantially impermeable to liquids. A typical outer cover 14 may be manufactured from a thin plastic film or other flexible liquid impermeable material. For example, outer cover 14 can be formed by a polyethylene film having a thickness of from about 0.012 millimeters to about 0.051 millimeters. When it is desirable that the outer cover 14 have a more clothlike feeling, it may comprise a polyethylene film laminated to a surface of a nonwoven web, such as a spunbonded web of polyolefin fibers. For example, a polyethylene film having a thickness of about 0.015 millimeters may have thermally or otherwise laminated thereto a spunbonded web of polyolefin fibers having a thickness from 1.5 to 2.5 denier per filament, which nonwoven web has a basis weight of about, 24 grams per square meter. Further, outer cover 14 can be formed of a woven or nonwoven fibrous web which has been totally or partially constructed or treated to impart a desired level of liquid impermeability to selected regions that are adjacent or proximate the absorbent core 18. Still further, outer cover 14 may optionally be composed of a micro-porous material which permits vapors to escape from the absorbent core and through outer cover 14 while preventing liquid exudates from passing through the outer cover.

Compression nip device 10 comprises first and second anvil rolls 16, 18 having a first nip 20. One of the rolls is driven by an external drive (not shown). Rolls 16, 18 press bodyside liner 12, absorbent care 13 and outer cover 14 against each other at nip 20, thereby securing liner 12, layer 13 and outer cover 14 to one another at nip 20, preferably by gluing. These three elements, when secured to each other, mutually form web sausage 22, with absorbent core 13 being between bodyside liner 12 and outer cover 14. Other known devices can also be utilized to form the web sausage 22. Bodyside liner 12 and outer cover 14 preferably have substantially the same dimensions. Bodyside liner 12 and outer cover 14 are preferably aligned so their outer edges substantially contact one another when web sausage 22 is formed. Absorbent articles are formed along a length of web sausage 22. Web sausage 22 comprises a continuous web sausage.

Web sausage 22 then enters die cutter 24 which cuts waist opening 30 and leg cut-outs 32. The cutting is done by knife roll 28 in combination with anvil roll 26. Knife roll 28 has knives (not shown) arranged in a pattern consistent with making the cut-outs illustrated in FIG. 2, including waist opening 30 in a central region and leg cut-outs 32. Preferably both leg cut-outs 32 on a given absorbent article precursor are made simultaneously by spaced knives (not shown). Absorbent core 13, preferably is not contacted by any knives (not shown) of die cutter 24. Preferably, none of the layers forming web sausage 22 contain elastomeric material.

As used herein, "elastomeric material" means material which can be stretched from about 50% to about 450% in one direction, and which will return to approximately its original dimensions when released. Preferably all of the material removed by die cutter 24 comprises unneeded non elastomeric material.

Cut-out web sausage 22 is then transferred to and supported by vacuum conveyor 34. Vacuum conveyor 34 preserves the shape of web sausage. 22 and facilitates consistent-material transfers and other operations performed on web sausage 22 as the web sausage traverses the path shown by arrow 75A along the bottom segment of the path traversed by belt 35. Arrow 756 shows the direction of travel of belt 35 along the top segment of the path traversed by belt 35. Conveyor belt 35 can comprise a singe belt or a plurality of belts traversing the path shown by arrows 75A, 75B. While a vacuum conveyor is shown in FIG. 1, other conveyors, including conveyors not dependent on vacuum, can be utilized to move web sausage 22 in a first direction. Roller to roller movement under tension can also be used to advance web sausage 22 along a path to a series of successive work stations.

Successive work stations include, but are not limited to leg cuff applicator 40, waist piece applicator 50, ear applicator 60, a containment flap applicator (not shown), an absorbent article cutting machine or the like. The work stations and conveyor 34 form part of a processing line that makes absorbent articles from web sausage 22.

When a given segment of web sausage 22 advances from die cutter 24 to leg cuff applicator 40, the leg cuff applicator applies leg cuffs 45 to each leg cut-out 32. The applicator includes variable velocity vacuum roll 46 having pucks that support leg cuffs 45, representatively illustrated in FIG. 1. Glue gun 42 supplies adhesive or glue to a continuous web of leg cuff material 43. The glue gun 42 is timed or registered to apply the glue to that portion of the leg cuff material 43 which becomes ends of leg cuffs 45. Continuous glue is applied to one side of each leg cuff 45 to form a side seam on web sausage 22.

In an alternative embodiment (not shown), glue gun 42 is positioned adjacent web sausage 22. Glue gun 42 is timed or registered to apply glue to opposite sides of web sausage 22 spanning leg cut-outs 32. Leg cuffs 45 are placed over web sausage 22 and secured thereto.

Idler roll 44 helps pre-feed/pre-wrap vacuum roll 46 and maintains substantially constant tension in leg cuff material 43. The variable rotational velocity of vacuum roll 46 is controlled to operate at a first rotational velocity whereby the speed of the outer segment of the roll substantially equals the speed of leg cuff material 43 when receiving a length of the leg cuff material onto the roll. The continuous web of leg cuff material 43 is then cut into individual leg cuffs 45 by a hot knife (not shown) on vacuum roll 46 and supported by vacuum on the vacuum roll.

Vacuum roll 46 supports the individual leg cuffs. The rotational velocity of the segments of roll 46 is changed such that the speed of the outer surface of the segments substantially equals the speed of web sausage 22 supported on conveyor belt 35. By matching the surface speed of the roll-to the speed of web sausage 22, proper transfer is effected. Vacuum roll 46 applies leg cuffs 45, such as by adhesive pressure, to web sausage 22.

Vacuum roll 46 can comprise the apparatus disclosed in patent application Ser. No. 08/381,362, titled "Method and Apparatus for Placing Discrete Parts onto a Moving Web" by Rajala et al. filed Jan. 31, 1995 and hereby incorporated by reference which discloses mechanisms for varying the speeds of rotation of the roll segments.

Individual leg cuffs 45, at least when stretched, have a length longer than the length of leg cut-outs 32. Prior to securement with web sausage 22, leg cuffs 45 preferably are prestretched or extended to a dimension representing about 5% to about 95% of their stretch-to-stop elongation, and most preferably 20% to 50% of their stretch-to-stop elongation. Leg cuffs 45 are placed over leg cut-outs 32 and secured to bodyside liner 12 in such partially stretched condition, with the bodyside liner extended preferably to its stretch-to-stop limit Ideally, the percent elongation of leg cuff 45 at securement to bodyside liner 12 is greater than the percent elongation of bodyside liner 12. Accordingly, leg cuffs 45 provide a degree of retraction properties different from the retraction properties of bodyside liner 12. Thus, at and adjacent the leg cut-outs 32, the absorbent article exhibits a first limited stretching ability as controlled by the outer cover and bodyside liner, and a second, more expansive stretching ability as enabled by the leg cuffs. The residual stretch provides for the absorbent article to better conform to the shape of a user's body.

The method of simply securing leg cuffs 45 to an existing outer surface of web sausage 22, such as to the outer surface of bodyside liner 12 or the outer surface of outer cover 14, is much simpler than the prior proposed method of attaching leg cuffs between both bodyside liner 12 and outer cover 14.

The web material used to make leg cuffs 45 can comprise, for example, a laminate including first and second outer nonwoven facing layers on opposing sides of an elastomeric core layer, the elastomeric core layer comprising a thermoplastic elastomeric composition such as a styrene ethylene butylene styrene terpolymer. The leg cuffs can be secured, in any combination, to bodyside liner 12 and/or outer cover 14.

Examples of other materials which may comprise the leg cuffs include, without limitation: spandex/nonwoven laminated webs, elastomeric meltblown webs, cross-machine direction stretchable web materials made with stretchable nonwovens, stretchable foam webs, and the like.

Waist piece applicator 50 includes a glue gun 52 which applies adhesive or glue to a continuous web of incoming waist piece material 53. Glue gun 52 is timed or registered to apply the adhesive or glue to waist piece material 53 that becomes the ends of waist to piece 55 after cutting.

In an alternative embodiment of the invention, glue gun 52 is positioned adjacent web sausage 22 and timed or registered to apply adhesive or glue about waist opening 32 of web sausage 22. Waist piece 55 is placed over waist opening 32 and secured thereto by the adhesive or glue. Securement preferably is around the perimeter of waist piece 55.

Idler roll 54 helps pre-feed variable velocity vacuum roll 56 and maintains substantially constant tension in waist piece material 53. As a given segment of the incoming web of waist piece material 53 approaches variable velocity segment of vacuum roll 56, the rotational velocity of variable velocity vacuum roll 56 is controlled to operate at a first rotational velocity whereby the speed of the segment of the roll substantially equals the speed of the incoming web of waist piece material when receiving a length of the waist piece material onto the roll. Vacuum draws the web to the surface of vacuum roll 56, and holds it there while a hot knife (not shown) cuts waist pieces 55 from the web of waist piece material 53.

With vacuum roll 56 supporting a waist piece 55, the rotational velocity of the segment of roll 56 is changed, such that the speed of the outer surface of the vacuum roll segment substantially equals the speed of web sausage 22 supported on conveyor belt 35. by matching the surface speed of the roll segment to the speed of web sausage 22, proper transfer is effected. Vacuum roll 56 applies waist piece 55, such as by adhesive pressure, to web sausage 22. Vacuum roll 56 ban comprise the apparatus disclosed in patent application Ser. No. 08/381,364, titled "Method and Apparatus for Placing Discrete Parts onto a Moving Web" by Rajala et al, filed Jan. 31, 1995 and hereby incorporated by reference which discloses mechanisms for varying the speeds of rotation of the roll segments.

Waist piece material 53 can be extended or stretched either before or after waist pieces 55 are cut from the material, but always before being transferred to web sausage 22. Waist pieces 55 have dimensions sufficiently large to cover at least one dimension of waist opening 30. Waist pieces 55 preferably are prestretched or extended to a dimension representing about 5% to about 95% of their stretch-to-stop elongation, and most preferably 20% to 50% of their stretch-to-stop elongation. Waist pieces 55 are placed over waist opening 30, and are secured to bodyside liner 12 in such partially stretched condition, with the bodyside liner preferably extended to its stretch-to-stop limit. At minimum, the percent elongation of leg cuff 45 at securement to bodyside liner 12 is greater than the percent elongation of bodyside liner 12. Accordingly, waist pieces 55 provide a degree of retraction property not provided by bodyside liner 12. The residual stretch provides for the absorbent article to better conform to the shape of a user's body. The adhesive or glue is present at the ends of waist piece 55 and on opposite sides of waist opening 30 when the waist piece is secured to web sausage 22.

Waist pieces 55 can be made from the same or similar materials as leg cuffs 45. Waist pieces 55, at least when stretched, have a length greater than the length of waist opening 30.

Ear applicator 60 cuts, and thereby creates, ears 62 from an incoming web of ear material 64 drawn across idler roll 65 from a supply roll (not shown), and transfers the ears to web sausage 22. Knife roll 66 rotates with transfer roll 63, cutting ear material 64 to create the ears. Elliptical rotary stomper 67 rotates about a central axis as shown by arrow 69. Rubber pucks 68 on rotary stomper 67 intermittently form a nip with transfer roll 63 while ears 62 are being secured to the web sausage. Then, rubber pucks 68 rotate out of contact with web sausage 22, then rotate back into such contact, to mount ears again when rotary stomper 67 has rotated about 180 degrees. The ears can be secured to web sausage 22 by glue or other methods.

Ears 62 preferably comprise mechanical fasteners such as hooks of a hook and loop fastening system mounted on outer cover 14. Cooperative attachment loop material or other fastener surface is provided at e.g. the outer surface (not shown) of outer cover 14 on e.g. the front portion of the absorbent article. The exemplary loop material is adapted to releasably engage with hook material on the respective ear. Other well known fastening systems can also be used to support the absorbent article on a user. For example, a cohesive system, an adhesive fastener system or the like may also be utilized to secure the absorbent article about the crotch and lower trunk portion of the user.

While FIG. 1 shows leg cuff applicator 40, followed by waist piece applicator 50, then followed by ear applicator 60, the order of the applicators is not critical, or important to the invention. Applicators 40, 50, 60 can be arranged in any order along belt 35 to apply the respective elements to web sausage 22.

Ultrasonic bonder 70 comprises the last element illustrated in the processing sequence after the conveyor 34.

Rotary ultrasonic horn 74 is biased against anvil roll 72, forming a nip between horn 74 and anvil roll 72. As web sausage 22 passes, rotary ultrasonic horn 74 vibrates, generating ultrasonic energy. The ultrasonic energy finishes and smoothens raw edges of the waist piece 55, leg cuffs 45, and the ears 62. The ultrasonic energy also smoothens unevenness in edges of leg cuffs 45, waist piece 55, and ears 62 due to their elasticity and unregistered perimeter gluing. Ultrasonic horn 74 typically has a pattern of dots forming a quilted pattern or look. This quilted pattern is formed by blending leg cuffs 45, waist piece 55, and ears 62 into web sausage 22 with the ultrasonic energy. This blending is necessary because the leg cuffs 45, waist piece 55, and ears 62 are mounted directly to bodyside liner 12 or outer cover 14 instead of in between the elements as in the past. This ultrasonic blending also prevents curt of leg cuffs 45 or waist piece 55, caused by their elasticity, from altering the appearance of the absorbent article. Thus, the absorbent articles have a smooth, finished look where leg cuffs 45, waist piece 55, and ears 62 are secured to web sausage 22.

The fully completed web sausage 22 is then removed from ultrasonic bonder 70. At another location, web sausage 22 is cut into a plurality of absorbent articles or workpieces. Web sausage 22 is severed across the waist piece, thereby severing, from the web sausage, an absorbent article including a respective one of front and rear portions of the waist piece, the remainder of the respective waist piece, including the respective remaining one of the front and rear portions, remaining with the web sausage, and forming a respective front or rear waist portion for the next successive absorbent article in the web sausage.

This cutting is done by any of a variety of well known cutting machines. For example, a final cut-off roll (not shown) having a knife (not shown) extending across the roll, in combination with an anvil roll (not shown) severs web sausage 22. There is preferably a gap about 0.25 inch wide between the cut-off roll and the anvil roll (not shown). The absorbent articles severed from web sausage 22 are transferred by conveyor to a stacker (not shown).

While the use of adhesives and ultrasonic finishing is the preferred method of securing elements to web sausage 22, other methods also exist. For instance, adhesives alone can be used to secure elements to sausage 22. Further, ultrasonic bonding alone, without any adhesive, can be used to secure elements to web sausage 22.

FIG. 3 shows a top view of an absorbent article 78 formed by absorbent article assembly system 8 of FIG. 1. Absorbent article 76 has waist piece 55, leg cuffs 45 and ears 62 applied or secured to the outer surface of bodyside liner 12, the outer surface of bodyside liner 12 also being an outer surface of absorbent article 76. Securing the elements 45, 55 and/or 62 to the outer surface of absorbent article 76 simplifies the process of attaching such elements, as compared to conventional thought which would attach leg cuffs, waistbands and ears at interior surfaces within the absorbent article.

In the embodiment shown in FIG. 3, extensible leg cuffs 45 are secured to bodyside liner 12 of absorbent article 76 at a preferred angle 78 of about 15 degrees with respect to longitudinal axis 80. The apex of the angle 78 is located toward the front of absorbent article 76 as shown in FIG. 3. While an angle 78 of between 0 degrees and 30 degrees is effective for applicants invention, a range for angle 78 of approximately 5 degrees to 25 degrees is preferred.

Mounting angle 78 of the leg cuff 45, and the soft stretchable nature of the material which forms the leg cuff, confer desirable properties to absorbent article 76. For example, angle 78 and the relatively narrow crotch width, in combination, attenuate the tendency of the front portion of absorbent article 76 to be pulled downward in response to movement of the user's legs. Angle 78 also improves the buttocks coverage and fit by conforming absorbent article 76 more closely to the shape of the user's body. The above factors all improve the ability of absorbent article 76 to provide a comfortable fit and effective seal around the user's legs. The preferred outward spacing of the outboard edge of leg cuffs 45 from the lateral edges of bodyside liner 12 also allow one to reduce the width of the crotch e.g. between lateral edges, whereby the lateral edges of. the bodyside liner and outer cover 14 play no direct role in forming a seal about the user's legs. Rather such seal is formed by leg cuffs 45. The soft stretchable nature of leg Cuffs 45 improves comfort for the user because the cuffs extend or stretch with movement of the users body or legs.

While FIG. 3 shows leg cuffs 45, waist piece 55, and ears 62 secured to bodyside liner 12, the above elements can be secured to outer cover 14 instead, or some to bodyside liner 12 and some to outer cover 14. The absorbent article would function essentially the same way, but the appearance of the product would differ. In most embodiments, waist piece 55 is severed into two separate elastic elements suggested by the dashed cut line 82 shown in FIG. 2, thereby severing individual absorbent articles 76 from web sausage 22. Dashed cut line 82 is across web sausage 22. Thus, waist piece 55 preferably is severed in a direction substantially transverse to the length of web sausage 22. Each absorbent article includes a front waist piece portion 55A and a rear waist piece portion 55B, derived from respective waist piece portions of web sausage 22. Front waist piece portion 55A extends across that portion of front waist opening portion 30A attendant the front edge of the absorbent article. Rear waist piece portion 55B extends across that portion of rear waist opening portion 30B attendant the rear edge of absorbent article 76. One of rear and front waist portions 55A, 55B remains with web sausage 22 after severing, until the next absorbent article is severed therefrom. In keeping with the resilient elasticity of the materials preferred for use as waist piece 55, waist piece portions 55A, 55B, in combination, provide comfortable resiliently stretchable elements for enhancing comfort and fit about the user's waist. Similarly, the resilient elasticity of the materials preferred for use as leg cuffs 45 provide comfortable, resiliently stretchable elements for enhancing comfort, fit, and seal about the user's legs.

Figure 4:
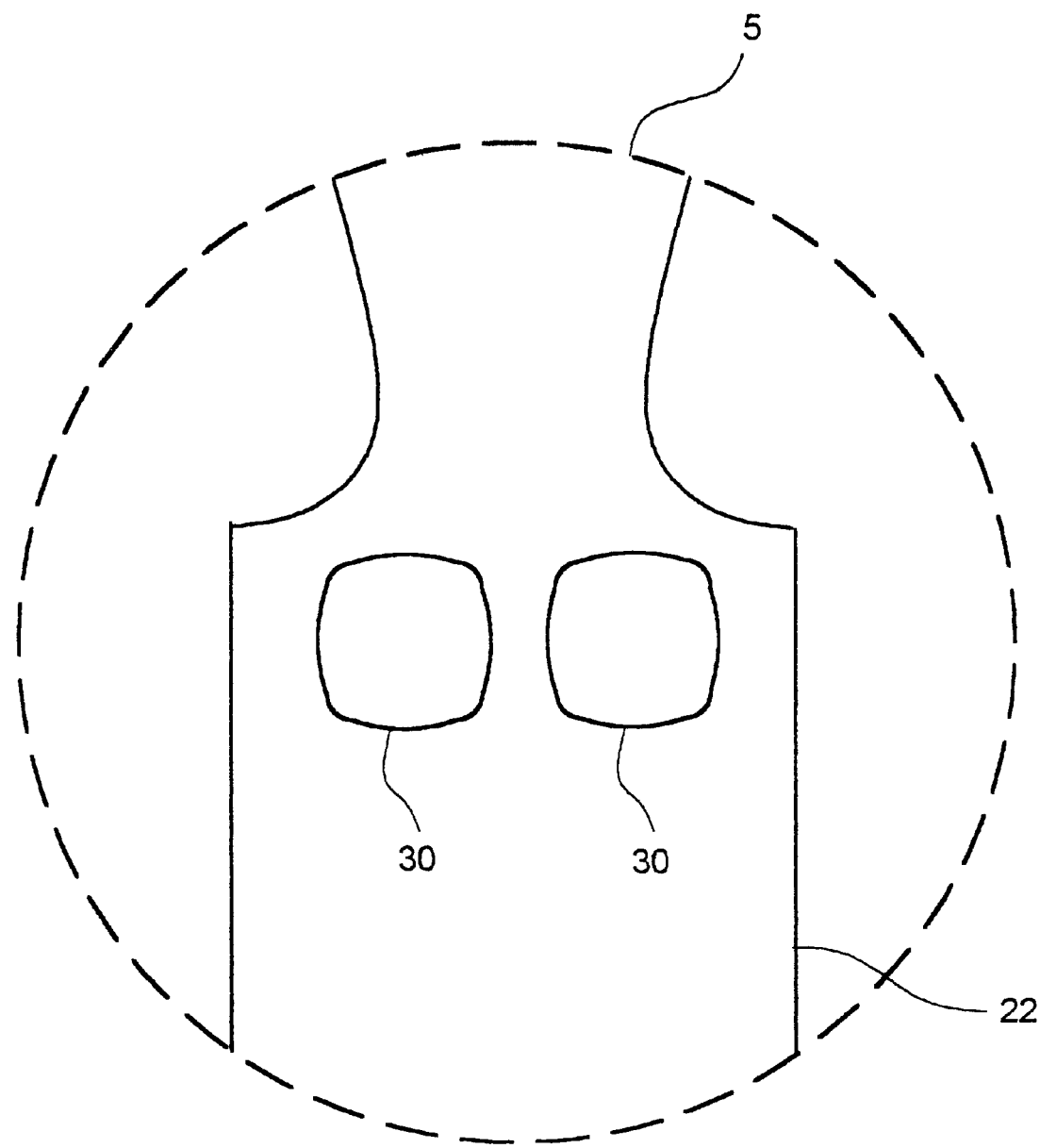
FIG. 4 shows an enlarged, modified view of a portion of the web sausage taken at 5 in FIG. 2.

While die cutter 24 cuts a single waist opening 30 in FIG. 2, the cutter can cut plural waist openings 30 in a central region as shown in FIG. 4. FIG. 4 shows first and second waist openings 30 aligned across the width of web sausage 22. Any number of waist openings are within the scope of the invention. The multiple waist openings 30 can be covered by a single workpiece. In the alternative, multiple waist pieces 55 can be used. For example, a separate waist piece 55 can be used for each opening 30. However, there can be fewer waist pieces than openings. For example, waist openings 30 in FIG. 4 can be covered by a single waist piece. As used herein, waist opening 30 can comprise one or more openings in web sausage 22. Waist opening 30 can be elliptical, rectangular, or any desired shape.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

Having thus described the invention, what is claimed is:

1. A method of making an absorbent article precursor comprising the steps of:
   (a) joining a bodyside liner, an absorbent core, and an outer cover to form an absorbent article web sausage;
   (b) cutting leg cut-outs on opposing sides of the web sausage and cutting waist openings in the web sausage;
   (c) applying adhesive to one of (i) a waist piece material, and (ii) the web sausage about the waist opening;
   (d) placing the waist piece material on a waist piece applicator and cutting a waist piece to a set of dimensions sufficiently large to cover a said waist opening;
   (e) placing the waist piece over the waist opening; and
   (f) securing the waist piece to the web sausage.

2. A method as in claim 1, including the step of supporting and moving the web sausage along a processing line on a conveyor from a first work station to a second work station to perform at least one step subsequent to step (a).

3. A method as in claim 1, including the steps of:
   (g) applying adhesive to one of (i) extensible leg cuff material, and (ii) the web sausage adjacent the leg cut-outs;
   (h) placing the extensible leg cuff material on a leg cuff applicator and cutting the extensible leg cuff material to sever extensible leg cuffs therefrom; and
   (i) placing the leg cuffs over the leg cut-outs.

4. A method as in claim 3, including repeating steps (b)–(f) for individual sections of the web sausage and severing respective absorbent articles from the web sausage and thereby making absorbent articles.

5. A method as in claim 1, the web sausage having a length, the method including the step of severing the web sausage in a direction substantially transverse to the length of the web sausage and across the waist piece, thereby severing, from the web sausage, an absorbent article including a portion of the waist piece, the remainder of the waist piece remaining with the web sausage.

6. A method as in claim 1, including cutting multiple said waist pieces from the waist piece material and placing ones of the waist pieces over spaced ones of the waist openings, the waist pieces being spaced from each other in the web sausage.

7. A method as in claim 6, including the step of stretching the waist pieces, and applying the waist pieces to the waist openings in the stretched condition.

8. A method as in claim 7, including applying the waist pieces to the waist openings while the waist pieces are stretched from about 5% to about 95% of the respective stretch-to-stop dimensions.

9. A method as in claim 1, the web sausage having a length thereof extending along a processing line for applying leg cuffs thereto, the method including placing the leg cuffs over spaced ones of the leg cut-outs, the leg cuffs being spaced from each other along the length of the web sausage on the processing line.

10. A method as in claim 9, including the step of stretching the leg cuffs, and applying the leg cuffs over the leg cut-outs in the stretched condition.

11. A method as in claim 9, including applying ultrasonic energy to the leg cuffs and the waist piece, thereby reducing unevenness in edges of the leg cuffs and the waist piece.

* * * * *